United States Patent [19]

Horrom et al.

[11] 4,097,597
[45] Jun. 27, 1978

[54] DIBENZO[B,E][1,4]DIAZEPINES

[75] Inventors: Bruce Wayne Horrom, Waukegan; Frederick Nelson Minard, Lake Bluff; Harold Elmer Zaugg, Lake Forest, all of Ill.

[73] Assignee: Abbott Laboratories, North Chicago, Ill.

[21] Appl. No.: 771,216

[22] Filed: Feb. 23, 1977

[51] Int. Cl.² .................... A61K 31/55; C07D 403/04
[52] U.S. Cl. .................... 424/250; 260/243.3
[58] Field of Search ............ 260/268 TR; 424/250

[56] References Cited
U.S. PATENT DOCUMENTS 3,796,725  3/1974  Yale et al. .................... 260/268 TR Primary Examiner—Jose Tovar
Attorney, Agent, or Firm—Paul D. Burgauer; Robert L. Niblack

[57] ABSTRACT

A compound represented by the formula

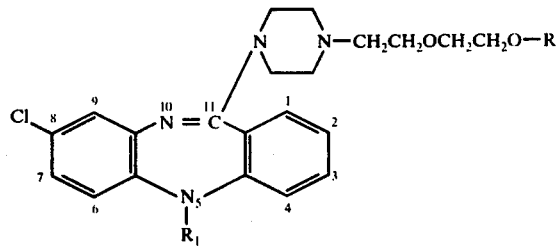

wherein R is H, loweralkyl, hydroxyloweralkyl or

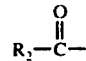

where $R_2$ is an alkyl group of 1 to 15 carbon atoms; and $R_1$ is H or

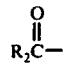

where $R_2$ is an alkyl group of 1 to 15 carbon atoms.

These compounds are useful as antischizophrenics.

18 Claims, No Drawings

DIBENZO[B,E][1,4]DIAZEPINES

DETAILED DESCRIPTION OF THE INVENTION

This invention relates to novel chemical compounds and processes of producing the same. More particularly, this invention relates to novel diazepines and the use of such compounds as antischizophrenics.

According to one aspect of the subject invention there are provided novel diazepine derivatives of the formula

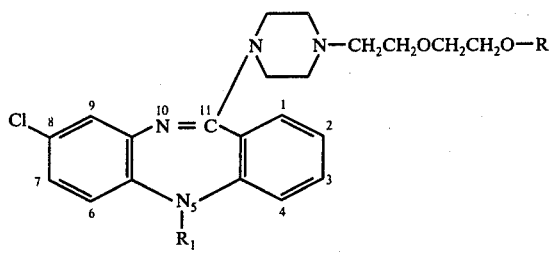

wherein R is H, loweralkyl, hydroxyloweralkyl or

where $R_2$ is an alkyl group of 1 to 15 carbon atoms; and $R_1$ is H or $$\underset{\|}{\overset{O}{R_2C-}}$$

where $R_2$ is an alkyl group of 1 to 14 carbon atoms.

As used herein, the term "loweralkyl" refers to a $C_1$ to $C_6$ alkyl group including methyl ethyl, n-propyl, iso-propyl, n-butyl, sec-butyl, tertiary-butyl, n-pentyl, iso-pentyl, neo-pentyl, n-hexyl and the like.

The term "alkyl" as used herein, refers to both straight and branched chain alkyl groups containing from 1 to 15 carbon atoms, including n-propyl, iso-propyl, n-butyl, sec-butyl, tertiary-butyl, n-pentyl, n-hexyl, 2-heptyl, n-heptyl, n-octyl, n-nonyl, and the like.

The term "hydroxyloweralkyl" refers to the defined loweralkyl groups substituted with a hydroxy radical.

The compounds of this invention exhibit central nervous system activity, particularly as an antischizophrenic in warm-blooded animals. The antischizophrenic activity is obtained at dosages of from 10 to 40 mg./kg. of body weight orally and from 10 to 20 mg./kg. body weight interperitoneally (i.p.).

The present compounds may be prepared by several techniques. Generally, as shown in Schemes (A), (B) and (C) below, the present 11-piperazinyl derivatives of the dibenzo[b,e][1,4]diazepines may be prepared by one of the methods (A), (B) or (C) described below. In all three methods, the 8-halo substituted dibenzo diazepinelactam (I) can be used as an intermediate to provide the desired product (III). In the schemes below, "R" and "$R_1$" are as defined above.

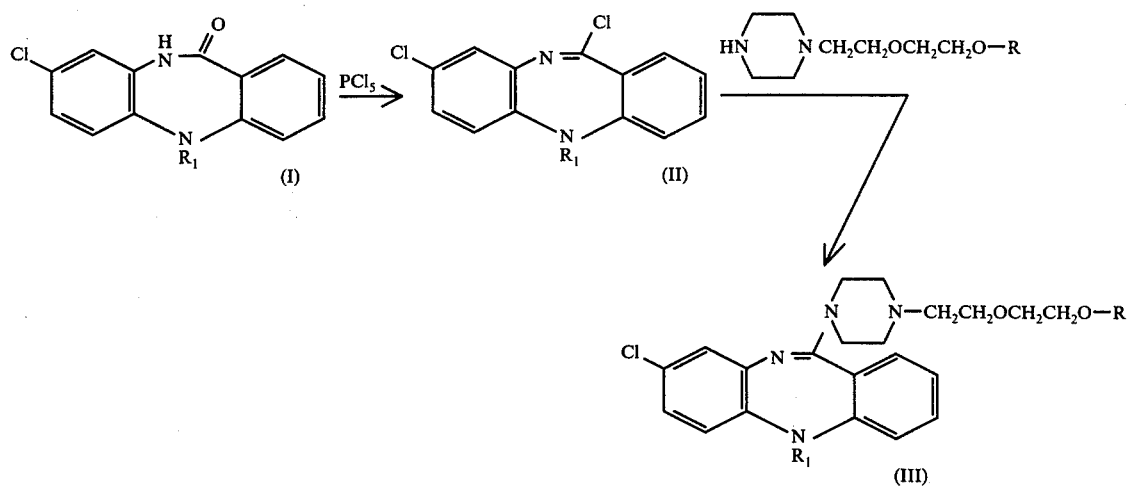

SCHEME (A)

SCHEME (B)

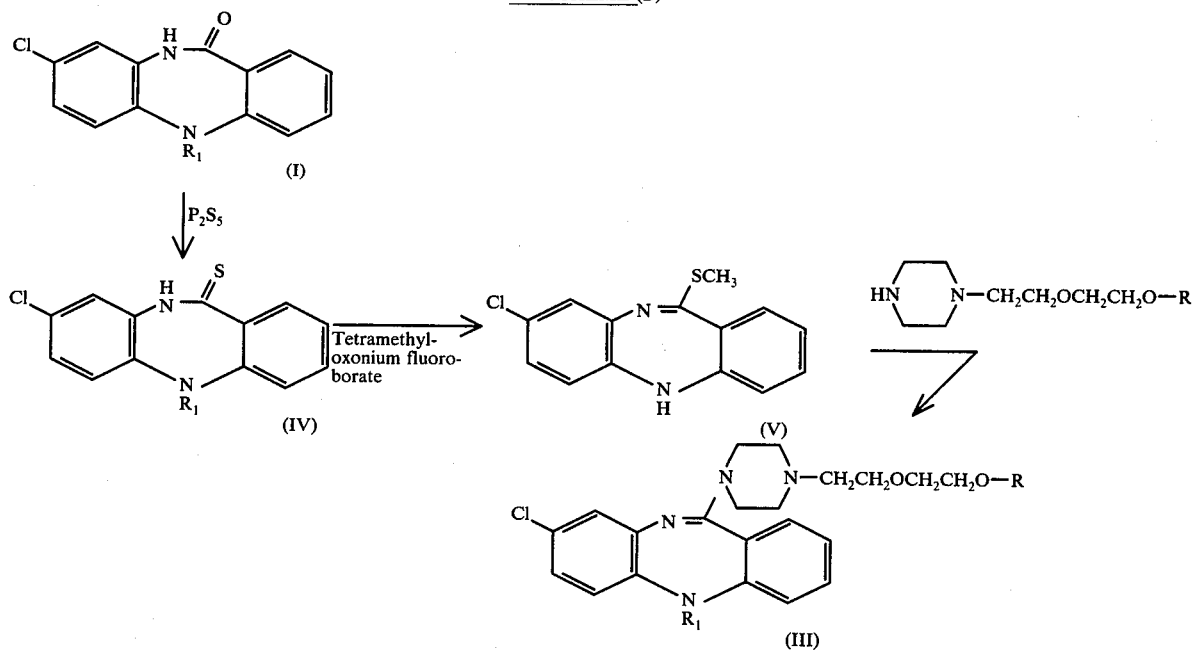

SCHEME (C)

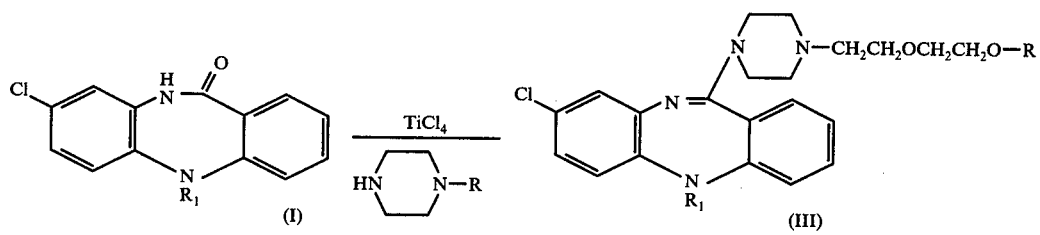

The methods as illustrated above in Schemes (A), (B) and (C) are:

Method (A)

As illustrated above, in this method, the dibenzodiazepine-lactam (I) is treated with a suitable halogenating agent such as thionyl chloride or phosphorous pentachloride and then the resulting imino-chloride (II) is reacted with the desired substituted piperazine to yield product (III).

Method (B)

In this method, as illustrated in Scheme (B) above, the lactam (I) is converted to the thiolactam (IV) with phosphorous pentasulfide, and then with a suitable alkylating agent, the thiolactam (IV) is converted to the desired imino-thio-ether (V) which is then reacted with the substituted piperazine to give product III.

Method (C)

In this method, as illustrated in Scheme C above, the dibenzo-diazepine-lactam (I) is reacted directly with complexes of the piperazine and titanium tetrachloride as a dehydrating agent to yield product III.

The compounds that are useful as antischizophrenics according to the present invention, include:

VI. 8-Chloro-11-[4-(2-2-hydroxyethoxyethyl)-1-piperazinyl]-5H-dibenzo[b,e][1,4]diazepine VII. 8Chloro-11-[4-(2-methoxy-ethoxyethyl)-piperazine]-5H-dibenzo[b,e][1,4]diazepine VIII. 8-Chloro-11-[4-(2-(2-hydroxy-ethoxyethoxyethyl)piperazinyl]-5H-dibenzo[b,e][1,4]diazepine IX. 8-Chloro-11-[4-(2-palmitoyloxy-ethoxyethyl)-piperazinyl]-5H-dibenzo[b,e][1,4]diazepine X. 8-Chloro-11-[4-(2-palmitoyloxy-ethoxyethyl)-piperazinyl]-5H-palmitoyl-dibenzo[b,e][1,4]diazepine The following examples will further illustrate the present invention.

EXAMPLE 1

8-Chloro-11-[4-2-(2-hydroxyethoxy)ethyl-1-piperazinyl]-5H-dibenzo[b,e][1,4]diazepine (VI)

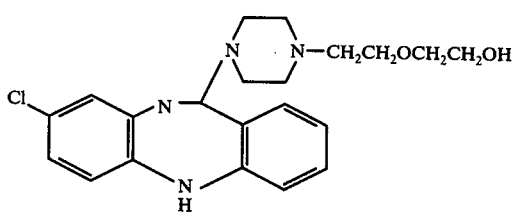

A mixture of 4.25 g. of phosphorous pentachloride and 2.45 g. of 8-chloro-10,11-dihydro-11-oxo-5H-dibenzo[b,e][1,4]diazepine in 200 cc of methylene chloride were refluxed for 1 hour. The solvent was then evaporated and the residue was azeotroped twice with dry benzene. The residue was dissolved in 150 cc of dioxane and treated with 12.0 grams of 1-hydroxyethoxyethyl piperazine in 100 cc of dioxane. The reaction mixture was heated at reflux for 3 hours. At the end of this time, the solvent was evaporated and the dark residue was dissolved in CHCl$_3$. The chloroform solution was washed two times with 50 cc H$_2$O, and extracted three times with 50 cc 10% HCl. The acid extracts were made basic with 50 cc 30% ammonium hydroxide and extracted with chloroform and the chloroform extracts were concentrated.

The material was chromatographed on 125 g. silica gel eluting with acetone.

The material was triturated with ether to give a yellow solid; m.p. 163°–165°.

Analysis Calcd. for C$_{21}$H$_{24}$ClN$_4$O$_2$: C, 62.91; H, 6.29; N, 13.98; Found: C, 63.26; H, 6.51; N, 13.86.

EXAMPLE 2

8-Chloro-11[4-2-(2-methoxyethoxy)-ethylpiperazine]-5H-dibenzo[b,e][1,4]diazepine (VII)

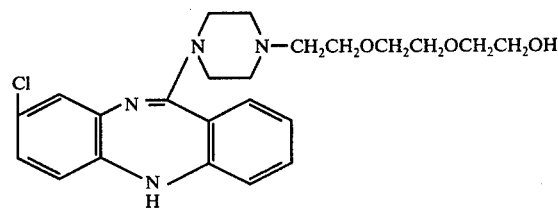

2.45 g. (0.010 mole) of 8-chloro-10,11-dihydro-11-oxo-5-dibenzo[b,e][1,4]diazepin were placed in a 500 ml. round bottom flask fitted with a magnetic stirrer bar and a condenser protected with a drying tube containing calcium chloride. Then, 200 ml. of dry methylene chloride was added to the flask. To this stirred suspension was added 2.45 g. (0.0118 mole) of phosphorus pentachloride rapidly in one portion. The mixture was stirred and refluxed for 1 hour. The methylene chloride was distilled off under reduced pressure in a warm water bath at 35° C. The dark viscous oil residue was concentrated further under vacuum pump pressure for ½ hour at room temperature.

The residue of imino choride was taken up in 150 ml. of dry dioxane and then 120 g. (0.069 mole) of 1-(1-piperazine)-2-(methoxy-ethoxy)ethane dissolved in 108 ml. of dioxane in a steady stream was added to the magnetically stirred solution of the imino chloride. The resulting mixture was stirred and refluxed for 3 hours. The dioxane was distilled off under reduced pressure at a water bath temperature of 45° C. The dark oil residue was taken up in a mixture of 150 ml. of chloroform and 50 ml. of water. The chloroform layer was separated and washed with 50 ml. of water. The chloroform solution was extracted 3 times with 50 ml. portions of 10% aqueous hydrochloric acid (by volume). The acidic extracts were combined and made strongly alkaline by the slow addition of 50 ml. of 30% ammonium hydroxide (by volume) and the basic mixture was extracted three times with 50 ml. portions of chloroform and the combined extracts were dried over anhydrous magnesium sulfate. The drying agent was filtered and the chloroform distilled off under reduced pressure. The oil residue was chromatographed over a column 4 feet in height and 2.5 cm. in diameter containing 150 g. of florisil 60-100 mesh using 98/2 chloroform-methanol solvent mixture. There was obtained 2.84 g. of product (oil); 68% yield, TLC showed one major component.

Analysis Calcd. for C$_{22}$H$_{27}$ClN$_4$O$_2$: C, 63.68; H, 6.56; N, 13.50; Found: C, 63.66; H, 6.69; N, 13.16.

EXAMPLE 3

8-Chloro-11-[4-2-(2-hydroxyethoxyethoxy)-ethylpiperazinyl]-5H-dibenzo[b,e][1,4]diazepine (VIII)

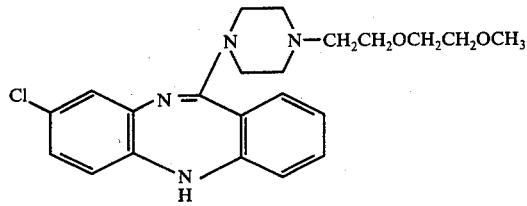

4.9 g. (0.020 mole) of 8-chloro-10,11-dihydro-11-oxo-5-dibenzo[b,c][1,4]diazepin were placed in a 1-liter round bottom flask fitted with a magnetic stirrer bar and a condenser protected with a drying tube containing calcium chloride. Then, 400 ml. of dry methylene chloride was added to the flask. To this stirred suspension was added 4.9 g. (0.0236 mole) of phosphorus pentachloride rapidly in one portion. The mixture was stirred and refluxed for 1 hour. The methylene chloride was distilled off under reduced pressure in a warm water bath at 35° C. The dark viscous oil residue was concentrated further under vacuum pump pressure for ½ hour at room temperature. The residue of imino chloride was taken up in 300 ml. of dry dioxane to which was added, in a steady stream, 30.1 g. (0.138 mole) of 1-(1-piperazinyl)-2-[2-(2-hydroxy-ethoxy)-ethoxy]ethane dissolved in 150 ml. of dioxane. The resulting mixture was stirred and refluxed for 5 hours. Then, the dioxane was distilled off under reduced pressure at a water bath temperature of 45°. The dark oil residue was taken up in a mixture of 250 ml. of chloroform and 75 ml. of water and then the chloroform layer was separated and washed with 75 ml. of water. The chloroform solution extracted three times with 75 ml. of 10% aqueous hydrochloric acid (by volume). Then, the acidic extracts were combined and made strongly alkaline by the slow addition of 75 ml. of 30% ammonium hydroxide (by volume) and the basic mixture was extracted three times with 75 ml. portions of chloroform. Then, the combined extracts were dried over anhydrous magnesium sulfate. The drying agent was filtered off and the chloroform was distilled off under reduced pressure. The crude oil residue (11.4 g.) was chromatographed over a column 4 feet in height and 2.5 cm. in diameters containing 225 g. of florisil 60-100 mesh using 98/2 chloroform-methanol solvent mixture. There was obtained 6.58 g. (74% yield) oil. The TLC showed one major component.

Analysis Calcd. for C$_{23}$H$_{29}$ClN$_4$O$_3$: C, 62.08; H, 6.57; N, 12.59; Found: C, 61.89; H, 6.71; N, 11.91.

EXAMPLE 4

8-Chloro-11-[4-2-(2-palmitoyloxyethoxy)-ethyl-piperazinyl]-5H-dibenzo[b,e][1,4]diazepine (IX)

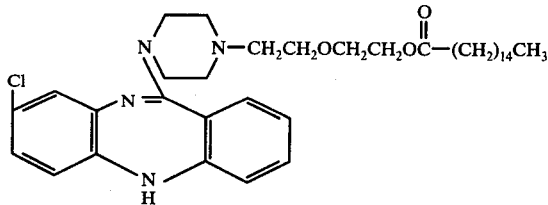

The solution of 8-chloro-11-[4-(2-ethoxyethanol)-1-piperazinyl]-5H-dibenzo[b,e][1,4]diazepine, palmitic acid and p-toluene sulfonic acid monohydride in dry xylene was refluxed for 18 hours. Then, the reaction mixture was made weakly alkaline by the addition of 30 ml. of 10% $Na_2CO_3$ solution. A solid separated immediately which was filtered off. The sodium salt of palmitic acid; m.p. 120° C. The salt was washed well with xylene. The filtrate, including the washings after drying over $MgSO_4$ was filtered and concentrated to dryness under reduced pressure. The semi-solid residue was obtained; weight, 2.7 g.

A sample of the crude product was placed on a TLC plate using 90/10 chloroform-methanol.

The crude product was triturated with 50 ml. of dry ether, and the solid filtered off; m.p. 161°-162° C., weight 74 g. When placed on a TLC plate using 90/10 $CHCl_3$—$CH_3OH$, the material showed one major component with same Rf value as the starting material (49% recovery).

Removal of the ether from the filtrate gave a semi-solid residue (weight, 1.45 g.). The 1.45 g. was taken up in 5 ml. of chloroform and placed on a column containing 60 g. of florisil (80 cm in height and 1.75 cm in diameter). The column was eluted with chloroform. The amount by volume (ml.) and weight (g.) of each of the fractions taken off from the column is listed below:

| Fraction No. | Volume | Weight |
| --- | --- | --- |
| 1 | 300 ml. | 0 |
| 2 | 100 ml. | 0 |
| 3 | 100 ml. | 0 |
| 4 | 50 ml. | .05g. |
| (Added 99/1 $CHCl_3$—$CH_3CH$) | | |
| 5 | 100 ml. | .05 g. |
| 6 | 100 ml. | .05 g. |
| 7 | 50 ml. | .05 g. |
| 8 | 100 ml. | .03 g. |
| 9 | 100 ml. | .052 g. (19%) |
| 10 | 100 ml. | .052 g. (19%) |
| 11 | 100 ml. | .052 g. (19%) |
| 12 | 100 ml. | .052 g. (19%) |
| 13 | 100 ml. | .052 g. (19%) |
| 14 | 100 ml. | .052 g. (19%) |

Each fraction was followed on TLC plates using 90/10 $CHCl_3$—$CH_3OH$.

A sample of the combined fractions of 9-14 was tested by infrared, NMR and micro-analysis. The infrared results and the spectrum were compatible for the desired structure showing the NH and the ester carbonyl.

Analysis Calcd. for $C_{37}H_{55}ClN_4O_3$: C, 69.51; H, 8.67; N, 8.76; Found: C, 69.30; H, 8.79; N, 7.83.

EXAMPLE 5

8-Chloro-11-[4-2-(2-palmitoyloxyethoxy)-ethyl-piperazinyl]-5-palmitoyl-dibenzo[b,e][1,4]diazepine (X)

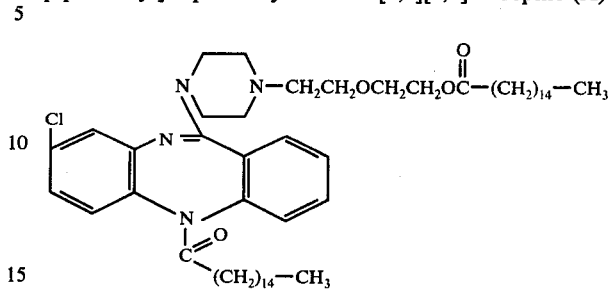

0.75 g. (0.00274 mole) of palmitoyl chloride was added to a mixture of 1.0 g. (0.00279 mole) of 8-chloro-11-[4-(2-hydroxyethoxyethyl)piperazinyl]-5H-dibenzo[b,e][1,4]diazepine and 0.22 g. (0.00274 mole) of pyridine in 25 ml. of dry toluene. The resulting mixture was stirred and refluxed for 5 hours. After being washed, the mixture was stirred for 15 minutes with 20 ml. of water and 5 ml. of 10% sodium carbonate solution. The toluene layer was separated and washed three times with 20 ml. portions of water and then dried over anhydrous magnesium sulfate. Then, the toluene was filtered and distilled off under reduced pressure to give a semi-solid residue (weight, 2.1 g.). The residue was triturated with 25 ml. of pentane and the recovered 8-chloro-11-[4-(2-hydroxyethoxyethyl)piperazinyl]-5H-dibenzo[b,e][1,4]-diazepine was filtered off; weight, 0.29 g. (29%); m.p. 162°-163°.

The removal of the pentane from the filtrate gave 1.4 g. of an amber oil. The material was chromatographed on a column 80 cm. in height and 1.75 cm. in diameter containing 50 g. of floricil 60-100 mesh using 98/2 chloroform-methanol solvent mixture. There was obtained 1.4 g. of product; 58% yield. The TLC showed one major component using 95/5 $CHCl_3$—$CH_3OH$.

Analysis Calcd. for $C_{53}H_{85}ClN_4O_4$: C, 72.52; H, 9.76; N, 6.38; Found: C, 72.23; H, 9.99; N, 6.11.

EXAMPLE 6

Effect of Drug Compounds on Brain Level of Homovanillic Acid (HVA)

In testing for the effectiveness of the present drug compounds on the brain level of homovanillic acid (HVA), the drugs were administered intraperitoneally to male Long Evans rats (Simonsen) usually as aqueous solutions but in certain cases as suspensions in 0.5% methocel in 0.9% saline. The standard testing dose was 0.15 mmoles/kg. body weight. The test and control groups consisted of 3-5 and 5 animals, respectively. The analyses were performed on brains (minus cerebella) removed 2 or 3 hours later. In the analysis, standard extraction and fluorimetric methods were used. The results of the analysis are set forth in the table below.

In the results, the level of brain HVA in each test group is expressed as a ratio to the level of HVA in an accompanying control group that was injected with either a 0.9% saline or a 0.5% solution of methocel. Even though ratios of less than 1.3 usually have statistical significance, only ratios greater than 1.6 are considered to be of practical significance for the pharmacological classification of drugs.

Table
EFFECT OF DRUG COMPOUNDS ON HVA LEVEL IN BRAIN OF RAT

| Compound | HVA Level in Control Group | HVA Ratio |
|---|---|---|
| VI | 1.0 | 2.8 |
| VII | 1.0 | 3.1 |
| VIII | 1.0 | 1.4 |
| IX | 1.0 | 1.0 |
| X | 1.0 | — |

EXAMPLE 7

Effectiveness of Drug Compound on Inhibiting Methamphetamine Antagonism in Rats

Male Long-Evans black hooded rats, weighing between 100 and 150 grams, were administered the test drugs at oral doses of 5, 20 and 80 mg./kg. 1 hour prior to the administration of Methamphetamine at an intraperitoneal dose of 1 mg./kg. Three animals were tested at each dose level. The rats were placed in individual activity chambers equipped with photocells (Lehigh Valley, Model 1497). Antagonism of Methamphetamine induced hyperactivity was recorded as digital counts received from the photocells at one and two hour intervals. Placebo controls received a volume dose of the 0.5 carboxymethylcellulose vehicle. The data were evaluated by a one-way analysis of variance computer program. $ED_{50}$'s were calculated by the method of Litchfield and Wilcoxon (*J. Pharmacol. Exp. Therap.;* 96:99, 1949).

The results of analyses are listed in the table below. In the results, a (+) indicates a potentiation of Methamphetamine and a (−) is antagonism of Methamphetamine.

Table
EFFECT OF DRUG COMPOUNDS ON MEPHAMPHETAMINE

| Compound | Oral $ED_{50}$ (mg./kg.) |
|---|---|
| VI | 60 (−) |
| VII | >80 (−) |
| VIII | >80 (−) |
| IX | >80 (−) |
| X | >80 (−) |

We claim:
1. A compound of the structure

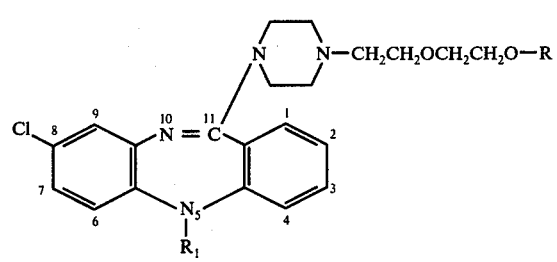

wherein R is H, loweralkyl, hydroxyloweralkyl or

where $R_2$ is an alkyl group of 1 to 15 carbon atoms; and $R_1$ is H or

where $R_2$ is an alkyl group of 1 to 15 carbon atoms.

2. A compound according to claim 1, wherein each of R and $R_1$ is H.

3. A compound according to claim 1, wherein R is $CH_3$ and $R_1$ is H.

4. A compound according to claim 1, wherein R is —$CH_2CH_2OH$ and $R_1$ is H.

5. A compound according to claim 1, wherein R is

where $R_2$ is a 15 carbon alkyl, and $R_1$ is H.

6. A compound according to claim 1, wherein each of R and $R_1$ is

where $R_2$ is a 15 carbon alkyl.

7. A composition of long lasting activity in the treatment of schizophrenics comprising as the active component a compound of the formula

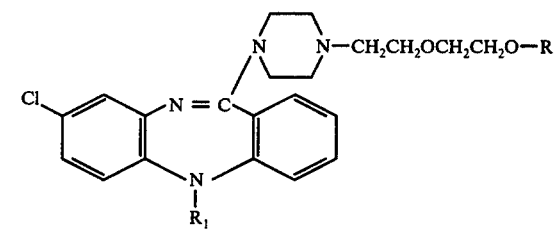

wherein R is H, loweralkyl, hydroxyloweralkyl or

where $R_2$ is an alkyl group of 1 to 15 carbon atoms; $R_1$ is H or

where $R_2$ is alkyl of 1 to 15 carbon atoms and a pharmaceutically acceptable carrier.

8. A composition according to claim 7, wherein each of R and $R_1$ is H.

9. A composition according to claim 7, wherein R is $CH_3$ and $R_1$ is H.

10. A composition according to claim 7, wherein R is —$CH_2CH_2OH$ and $R_1$ is H.

11. A composition according to claim 7, wherein R is

where $R_2$ is a 15 carbon alkyl and $R_1$ is H.

12. A composition according to claim 7, wherein each of R and $R_1$ is

where $R_2$ is a 15 carbon alkyl.

13. A method of treating a schizophrenic patient comprising administering to said patient a therapeutic amount of a compound of the formula

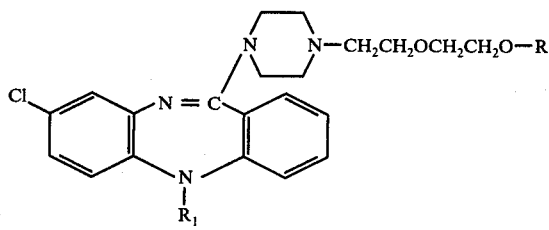

wherein R is H, loweralkyl, hydroxyloweralkyl or

where $R_2$ is an alkyl of 1 to 15 carbon atoms; and $R_1$ is H or

where $R_2$ is an alkyl of 1 to 15 carbon atoms, said compound being combined with a suitable pharmaceutical carrier.

14. A method according to claim 13, wherein each of R and $R_1$ is H.

15. A method according to claim 13, wherein R is $CH_3$ and $R_1$ is H.

16. A method according to claim 13, wherein R is $-CH_2CH_2OH$ and $R_1$ is H.

17. A method according to claim 13, wherein R is

where $R_2$ is a 15 carbon alkyl and $R_1$ is H.

18. A method according to claim 13, wherein each of R and $R_1$ is

where $R_2$ is a 15 carbon alkyl.

* * * * *